United States Patent [19]
Peglion et al.

[11] Patent Number: 5,389,644
[45] Date of Patent: Feb. 14, 1995

[54] 1,4-DIHYDROPYRIDINE COMPOUNDS

[75] Inventors: Jean-Louis Peglion, le Vesinet; Ghanem Aasssi, Saint Cloud; Alain Pierre, Marly le Roi; Laurence Kraus-Berthier, Colombes; Nicolas Guilbaud, Paris; Jean-Paul Vilaine, Chatenay Malabry, all of France

[73] Assignee: Adir et Compagnie, Courbevoie, France

[21] Appl. No.: 13,297

[22] Filed: Feb. 4, 1993

[30] Foreign Application Priority Data

Feb. 5, 1992 [FR] France ................................ 92 01266

[51] Int. Cl.⁶ ..................... A61K 31/44; C07D 211/90
[52] U.S. Cl. ..................................... 514/307; 514/314; 514/321; 514/332; 514/336; 514/338; 514/339; 514/356; 546/147; 546/174; 546/263; 546/270; 546/271; 546/273; 546/284; 546/321
[58] Field of Search ............... 546/321, 147, 174, 263, 546/270, 271, 273, 284; 514/356, 307, 314, 332, 336, 338, 339

[56] References Cited

U.S. PATENT DOCUMENTS 4,870,091  9/1989  Peglion et al. ..................... 546/321

FOREIGN PATENT DOCUMENTS

| 0221382 | 5/1987 | European Pat. Off. . |
| 0259206 | 3/1988 | European Pat. Off. . |
| 0270926 | 6/1988 | European Pat. Off. . |
| 0359377 | 3/1990 | European Pat. Off. . |
| 0406502 | 1/1991 | European Pat. Off. . |
| 0419297 | 3/1991 | European Pat. Off. . |

Primary Examiner—Bernard Dentz
Attorney, Agent, or Firm—Gordon W. Hueschen

[57] ABSTRACT

The compounds are 2,4-disubstituted 3-ethoxycarbonyl 5-methoxycarbonyl 6-methyl 1,4-dihydropyridines in their dextrorotatory form, useful to potentiate the activity of cytotoxic agents and to increase the sensitivity of tumor cells to antitumor agents.

A compound disclosed is d-2-{[2-(2-(N-p-nitrobenzylamino)ethoxy)ethoxy]methyl}-4-(2,3-dichlorophenyl)-3-ethoxycarbonyl-5-methoxycarbonyl-6-methyl-1,4-dihydropyridine.

13 Claims, No Drawings

1,4-DIHYDROPYRIDINE COMPOUNDS

The present invention relates to new 1,4-dihydropyridine compounds, a process for their preparation and pharmaceutical compositions containing them.

It relates especially to 1,4-dihydropyridine compounds of formula I:

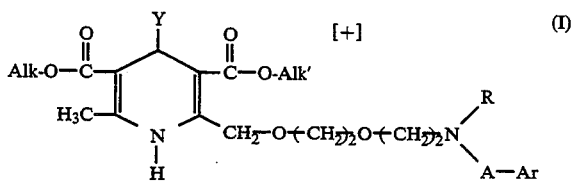

wherein:
Y represents a phenyl radical that is optionally substituted by from 1 to 5 identical or different substituents each being a halogen atom, such as, for example, a chlorine or fluorine atom, an alkoxy or alkylthio radical each having from 1 to 4 carbon atoms, a trihalomethyl radical or a methylenedioxy radical;

Alk and Alk', which are the same or different, each represents a straight-chain or branched alkyl radical having from 1 to 5 carbon atoms;

R represents a hydrogen atom, a straight-chain or branched alkyl radical having from 1 to 5 carbon atoms, or a straight-chain or branched alkenyl or alkynyl radical each having from 3 to 5 carbon atoms;

A represents:
a —$(CH_2)_m$— chain in which m is an integer of from 1 to 5, optionally substituted by a straight-chain or branched alkyl radical having from 1 to 5 carbon atoms, or by a straight-chain or branched alkenyl or alkynyl radical each having from 2 to 5 carbon atoms, and simultaneously Ar represents:
a) a phenyl radical that is optionally substituted by one or more halogen atoms or trifluoromethyl, nitro or cyano radicals or alkoxycarbonyl radicals having from 2 to 6 carbon atoms or alkylthio radicals having from 1 to 5 carbon atoms,
b) a thienyl, pyridyl, naphthyl, quinolyl, isoquinolyl, indolyl, N-methylindolyl, benzofurazanyl or benzo-2,1,3-thiadiazolyl radical,
or
the whole of —A—Ar represents a dibenzo[a,d]cyclohept-5-yl radical;

in the form of the dextrorotatory isomer, and their physiologically tolerable addition salts.

It is known from the prior art that 1,4-dihydropyridines principally have pharmacological properties in respect of the cardiovascular system, since they inhibit the influx of calcium which passes through the calcium channels to the interior of vascular smooth muscle cells (calcium channel blockers), and are therefore used as medicaments for hypertension and angina pectoris.

On the other hand, U.S. Pat. No. 4,690,935 mentions that 1,4-dihydropyridines such as nimodipine or nifedipine exhibit antitumour properties, and EP Patent No. 221 382 stipulates that those same 1,4-dihydropyridines, in combination with a platinum coordination compound, permit the treatment of tumours.

However, the 1,4-dihydropyridines forming the subject of those patents above all possess powerful calcium channel-blocking properties, rendering them difficult to use in antitumour therapy since their effects on the cardiovascular system are too pronounced.

EP Patents Nos. 270 926 and 359 377 relate to 1,4-dihydropyridines that can be used in antitumour therapy and have very low calcium channel-blocking properties, the 1,4-dihydropyridines being substituted in the 4-position not by a benzene nucleus but by heterocyclic radicals of the pyrazolo[1,5a]pyrid-3-yl (cf. EP Patent No. 270 926) or 5,6-dihydro-p-dioxin-2-yl and 3-methyl-5,6-dihydro-1,4-dithin-2-yl type (cf. EP Patent No. 359 377).

EP Patents Nos. 0 259 206, 0 419 297 and 0 406 502 claim 1,4-dihydropyridines having strong calcium channel-blocking properties that confer on the said molecules powerful cardiovascular properties associated with a weak ability to circumvent the resistance of cancer cells for use in the treatment of cancer.

Intensive research in the Departments of the Applicant has resulted in the compounds forming the subject of the present invention, which differ from the closest compounds of the prior art not only in their structure but also in their specific and favourable activity with respect to the reversal of resistance of tumour cells to chemotherapy.

Indeed, the compounds of the present invention increase very significantly the sensitivity of tumour cells to antitumour agents as well as the sensitivity of tumour cells that have acquired a resistance to different anticancer agents (or multidrug resistance), but at the same time exhibit only weak calcium channel-blocking properties, which suppresses their pharmacological hypotensive effect and makes it possible for them to be used in anticancer therapy without causing undesirable side effects.

The present invention relates also to a process for the preparation of compounds of formula I which is characterised in that the dextrorotatory isomer of the primary amine of formula II:

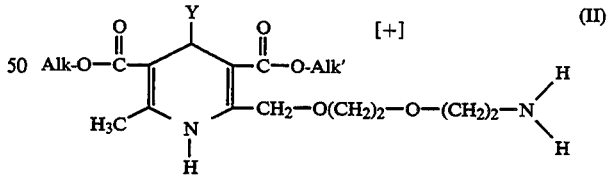

(wherein Y, Alk and Alk' are as defined hereinbefore) is converted into the dextrorotatory isomer of the corresponding secondary or tertiary amine of formula I.

That conversion is carried out according to conventional methods employed in organic chemistry to obtain secondary and tertiary amines from corresponding primary amines. It is, however, especially advantageous to proceed as described below.

In order to obtain the dextrorotatory amine of formula I wherein —A—Ar represents the dibenzo[a,d]cyclohept-5-yl radical, that is to say to obtain compounds corresponding more precisely to formula Ia:

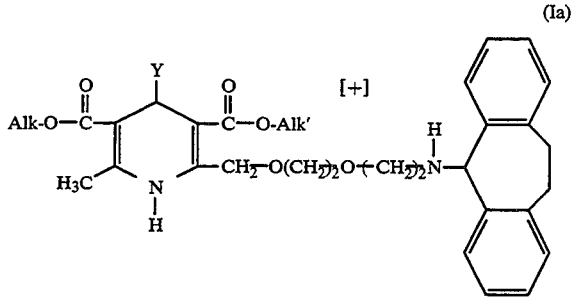

wherein Y, Alk and Alk' are as defined hereinbefore, the conversion of the dextrorotatory isomer of the primary amine of formula II is carried out by means of the agent of formula IIIa:

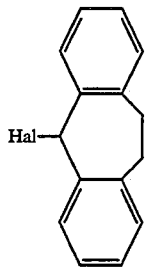

wherein Hal represents a halogen atom.

The reaction is especially advantageously carried out in an appropriate solvent, such as, for example, methyl cyanide or dimethylformamide, in the presence of an acceptor for the halo acid formed during the course of the reaction, the acceptor being an alkaline agent, such as, for example, an alkali metal or alkaline earth metal carbonate, such as potassium carbonate.

In order to obtain the dextrorotatory isomer of compounds I corresponding more precisely to formula Ib:

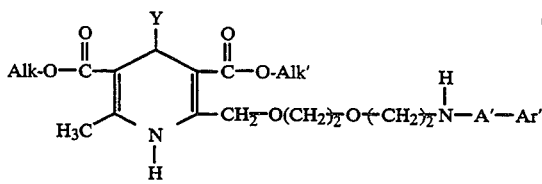

[wherein Y, Alk and Alk' are as defined hereinbefore and

A' represents:

a $(CH_2)_m$ chain in which m is an integer of from 1 to 5, optionally substituted by a straight-chain or branched alkyl radical having from 1 to 5 carbon atoms, or by a straight-chain or branched alkenyl or alkynyl radical each having from 2 to 5 carbon atoms, and simultaneously Ar' represents:

a) a phenyl radical that is optionally substituted by one or more halogen atoms or trifluoromethyl, nitro or cyano radicals or alkoxycarbonyl radicals having from 2 to 6 carbon atoms or alkylthio radicals having from 1 to 5 carbon atoms, or b) a thienyl, pyridyl, naphthyl, quinolyl, isoquinolyl, indolyl, N-methylindolyl, benzofurazanyl or benzo-2,1,3-thiadiazolyl radical], the conversion of the dextrorotatory isomer of the primary amine of formula II is carried out by means of the agent of formula III b:

in which:

Ar' is as defined hereinbefore, and

A" represents a $(CH_2)_{m-1}$ chain in which m is an integer of from 1 to 5, optionally substituted by a straight-chain or branched alkyl radical having from 1 to 5 carbon atoms, or by a straight-chain or branched alkenyl or alkynyl radical each having from 2 to 5 carbon atoms, the conversion advantageously being carried out in an appropriate solvent, such as, for example, ethanol, in the presence of $NaBH_4$.

The secondary amines of formulae Ia and Ib obtained above are, if desired, alkylated by means of an appropriate alkylating agent to obtain the corresponding tertiary amines of formulae Ic and Id below:

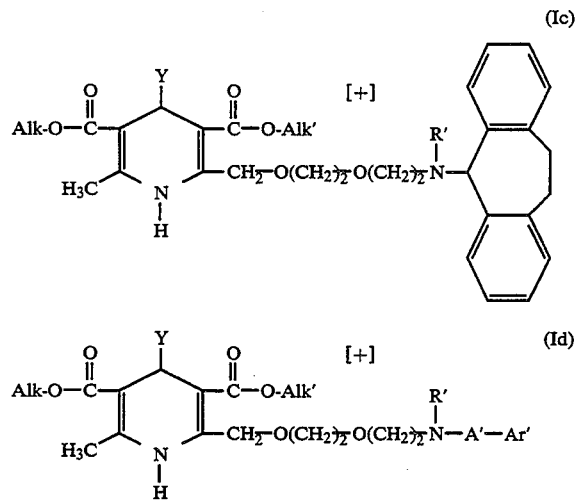

wherein in each of the formulae:

Y, Alk, Alk', A' and Ar' are as defined hereinbefore, and

R' represents a straight-chain or branched alkyl radical having from 1 to 5 carbon atoms, or a straight-chain or branched alkenyl or alkynyl radical each having from 3 to 5 carbon atoms (that is to say, R' has the same meaning as R with the exception of a hydrogen atom).

The alkylation of compounds Ia and Ib is carried out in an especially expedient manner:

either by condensing compounds Ia and Ib with an agent of formula IV:

wherein:

R" represents a straight-chain or branched alkyl radical having from 1 to 4 carbon atoms, or a straight-chain or branched alkenyl or alkynyl radical each having from 2 to 4 carbon atoms, then reducing the amide so obtained using, for example, LiAlH$_4$, to obtain compounds of formulae Ic$_1$ and Id$_1$:

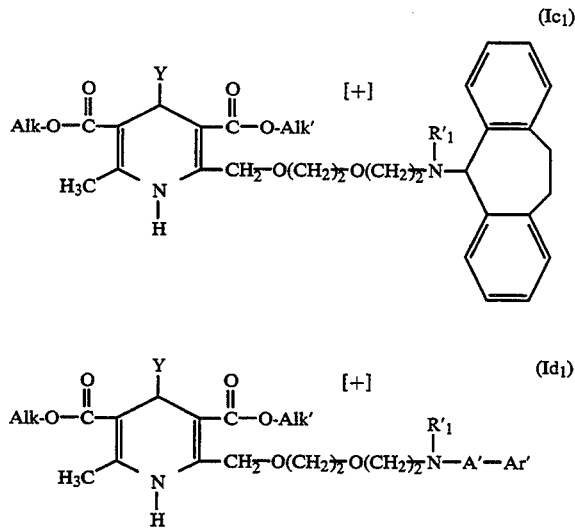

wherein:

Y, Alk, Alk', A' and Ar' are as defined hereinbefore and

R$_1$ represents a straight-chain or branched alkyl radical having from 2 to 5 carbon atoms, or a straight-chain or branched alkenyl or alkynyl radical each having from 3 to 5 carbon atoms;

or by reacting compounds Ia and Ib with formic acid and formaldehyde or methyl phosphate at a temperature of from 60° to 100° C. to obtain compounds of formulae Ic$_2$ and Id$_2$:

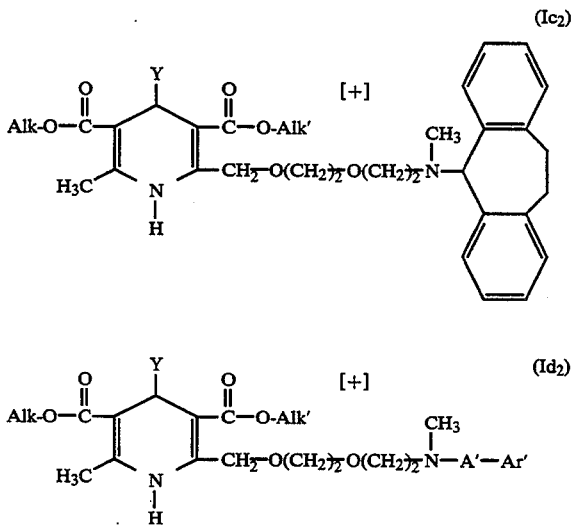

wherein:

Y, Alk, Alk', A' and Ar' are as defined hereinbefore.

The entirety of the compounds Ic$_1$, Id$_1$, Ic$_2$ and Id$_2$ form the entirety of compounds Ic and Id, and the entirety of the compounds of formulae Ia, Ib, Ic and Id form the entirety of the compounds of formula I.

The starting materials of formula II used to synthesise compounds I are known products (cf. European Patent Application published under the number 0 419 297).

The compounds of formula I can be converted into acid addition salts with acids, which salts, as such, form part of the present invention. There may be mentioned as acids that can be used for the formation of those salts, for example, in the mineral series, hydrochloric, hydrobromic, sulphuric, nitric and phosphoric acid and, in the organic series, acetic, propionic, maleic, fumaric, tartaric, oxalic, benzoic, methanesulphonic, benzenesulphonic, isethionic acid and ethanedioic acid monoethyl ester.

The compounds I can be purified by conventional physical and chemical methods.

The compounds of formula I and the physiologically tolerable addition salts have valuable pharmacological and therapeutic properties; in particular they potentiate the activity of cytotoxic agents and they increase very significantly the sensitivity of tumour cells to antitumour agents—and more especially the sensitivity of tumour cells that have acquired a resistance to various anticancer agents—but at the same time they exhibit only weak calcium channel-blocking properties, which makes it possible for them to be used in anticancer therapy without causing undesirable side effects.

The present invention also relates to pharmaceutical compositions comprising as active ingredient a compound of formula I or a physiologically tolerable salt thereof, mixed with or in association with an appropriate pharmaceutical excipient.

The so-obtained pharmaceutical compositions are generally presented in dosage form and may contain from 10 to 500 mg of active ingredient.

They may be in the form of tablets, dragees, gelatin capsules, suppositories or injectable or drinkable solutions, and may be administered by the oral, rectal, intravenous or parenteral route.

The dosage varies in accordance with the age and weight of the patient, the route of administration, the nature of the disorder and associated treatments, and generally ranges from 10 to 500 mg from 1 to 4 times per day.

The following Examples illustrate the present invention; unless indicated otherwise, the melting points are determined using a Kofler hot plate.

EXAMPLE 1 d-2-{[2-(2-(N-p-nitrobenzylamino)ethoxy)ethoxy]methyl}-4-(2,3-dichlorophenyl)-3-ethoxycarbonyl-5-methoxycarbonyl-6-methyl-1,4-dihydropyridine

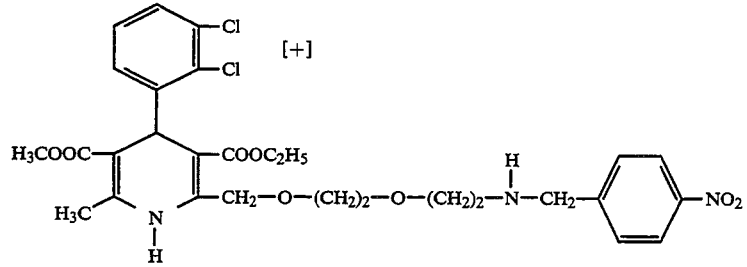

0.01 mol of d-2-{[2-(2-aminoethoxy)ethoxy]methyl}-4-(2,3-dichlorophenyl)-3-ethoxycarbonyl-5-methoxycarbonyl-6-methyl-1,4-dihydropyridine, 0.01 mol of p-nitrobenzaldehyde and 30 ml of ethanol are heated at reflux for 2 hours with stirring.

When the reaction mixture has returned to room temperature, 0.01 mol of sodium borohydride are added in portions with stirring.

The whole is left in contact overnight with stirring, and is then diluted with 4 volumes of water and extracted with ethyl acetate.

The evaporated residue is subjected to flash chromatography (eluant:ethyl acetate), yielding a pale-yellow oil which is d-2-{[2-(2-(N-p-nitrobenzylamino)ethoxy)ethoxy]methyl}-4-(2,3-dichlorophenyl)-3-ethoxycarbonyl-5-methoxycarbonyl-6-methyl-1,4-dihydropyridine.

0.01 mol of the base so obtained and 0.01 mol of ethanedioic acid monoethyl ester are intimately mixed in a bain-marie at 100° C. for 15 minutes. Solidification is observed. The product obtained is recrystallised from acetonitrile to yield the monoethyl oxalate of the [+] isomer of 2-{[2-(2-(N-p-nitrobenzylamino)ethoxy)ethoxy]methyl}-4-(2,3-dichlorophenyl)-3-ethoxycarbonyl-5-methoxycarbonyl-6-methyl-1,4-dihydropyridine, melting at 146°-148° C.

Index of rotation ([c]$^{21°}$ $^{C.}$=1% in DMSO):

| λnm | α° |
|---|---|
| 589 | +24.0 |
| 578 | +25.7 |
| 546 | +32.2 |

EXAMPLES 2 TO 27

By applying the method of preparation described in Example 1, the following compounds were obtained:

2) d-2-{[2-(2-(N-m-nitrobenzylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate, m.p.: 136°-138° C. (methyl cyanide).

Index of rotation ([c]$^{21°}$ $^{C.}$=1% in DMSO):

| λnm | α° |
|---|---|
| 589 | +28.8 |
| 578 | +30.7 |
| 546 | +38.6; |

3) d-2-{[2-(2-(N-o-nitrobenzylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate, m.p.: 130°-132° C. (methyl cyanide).

Index of rotation ([c]$^{21°}$ $^{C.}$=1% in DMSO):

| λnm | α° |
|---|---|
| 589 | +27.4 |
| 578 | +29.3 |
| 546 | +36.6; |

4) d-2-{[2-(2-(N-p-fluorobenzylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate, m.p.: 147°-149° C. (methyl cyanide).

Index of rotation ([c]$^{21°}$ $^{C.}$=1% in DMSO):

| λnm | α° |
|---|---|
| 589 | +28.7 |
| 578 | +30.5 |
| 546 | +38; |

5) d-2-{[2-(2-(N-m-fluorobenzylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate, m.p.: 151°-153° C. (methyl cyanide).

Index of rotation ([c]$^{21°}$ $^{C.}$=1% in DMSO):

| λnm | α° |
|---|---|
| 589 | +29.1 |
| 578 | +31 |
| 546 | +38.5; |

6) d-2-{[2-(2-(N-o-fluorobenzylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate, m.p.: 166°-168° C. (methyl cyanide).

Index of rotation ([c]$^{21°}$ $^{C.}$=1% in DMSO):

| λnm | α° |
|---|---|
| 589 | +29.7 |
| 578 | +31.3 |

-continued

| λnm | α° |
|---|---|
| 546 | +39; |

7) d-2-{[2-(2-(N-p-trifluoromethylbenzylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate, m.p.: 138°–140° C. (isopropyl ether).
Index of rotation ([c]$^{21°}$ $^{C.}$=1% in DMSO):

| λnm | α° |
|---|---|
| 589 | +21.0 |
| 578 | +22.4 |
| 546 | +28.1; |

8) d-2-{[2-(2-(N-p-cyanobenzylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate, m.p.: 152°–158° C. (methyl cyanide).
Index of rotation ([c]$^{20.5°}$ $^{C.}$=1% in DMSO):

| λnm | α° |
|---|---|
| 589 | +28.5 |
| 578 | +30.7 |
| 546 | +38.3; |

9) d-2-{[2-(2-(N-p-methylthiobenzylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate, m.p.: 141°–143° C.
Index of rotation ([c]$^{21°}$ $^{C.}$=1% in DMSO):

| λnm | α° |
|---|---|
| 589 | +28.2 |
| 578 | +30.2 |
| 546 | +37.4; |

10) d-2-{[2-(2-(N-p-ethoxycarbonylbenzylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate, m.p.: 120°–123° C. (methyl cyanide).
Index of rotation ([c]$^{21°}$ $^{C.}$=1% in DMSO):

| λnm | α° |
|---|---|
| 589 | +26.8 |
| 578 | +28.5 |
| 546 | +35.4; |

11) d-2-{[2-(2-(N-naphth-1-ylmethylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate, m.p.: 140°–142° C. (methyl cyanide).
Index of rotation ([c]$^{21°}$ $^{C.}$=1% in DMSO):

| λnm | α° |
|---|---|
| 589 | +28.6 |
| 578 | +30.5 |

| λnm | α° |
|---|---|
| 546 | +37.8; |

12) d-2-{[2-(2-(N-naphth-2-ylmethylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate, m.p.: 150°–152° C. (methyl cyanide).
Index of rotation ([c]$^{21°}$ $^{C.}$=1% in DMSO):

| λnm | α° |
|---|---|
| 589 | +28.7 |
| 578 | +30.7 |
| 546 | +38.1; |

13) d-2-{[2-(2-(N-thien-2-ylmethylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate, m.p.: 154°–156° C. (methyl cyanide).
Index of rotation ([c]$^{21°}$ $^{C.}$=1% in DMSO):

| λnm | α° |
|---|---|
| 589 | +30.6 |
| 578 | +32.8 |
| 546 | +40.7; |

14) d-2-{[2-(2-(N-thien-3-ylmethylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate, m.p.: 151°–153° C. (methyl cyanide).
Index of rotation ([c]$^{21°}$ $^{C.}$=1% in DMSO):

| λnm | α° |
|---|---|
| 589 | +30.5 |
| 578 | +32.6 |
| 546 | +40.5; |

15) d-2-{[2-(2-(N-pyrid-4-ylmethylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate, m.p.: 138°–140° C. (methyl cyanide).
Index of rotation ([c]$^{21°}$ $^{C.}$=1% in DMSO):

| λnm | α° |
|---|---|
| 589 | +29.6 |
| 578 | +31.5 |
| 546 | +37; |

16) d-2-{[2-(2-(N-pyrid-2-ylmethylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate, m.p.: 124°–126° C. (methyl cyanide).
Index of rotation ([c]$^{21°}$ $^{C.}$=1% in DMSO):

| λnm | α° |
|---|---|
| 589 | +32.4 |
| 578 | +34.6 |

| λnm | α° |
| --- | --- |
| 546 | +42.3; |

17) d-2-{[2-(2-(N-pyrid-3-ylmethylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate, m.p.: 164°–166° C. (methyl cyanide).

Index of rotation ($[c]^{21°}$ C. = 1% in DMSO):

| λnm | α° |
| --- | --- |
| 589 | +32.3 |
| 578 | +34.4 |
| 546 | +42.0; |

18) d-2-{[2-(2-(N-quinol-4-ylmethylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate, m.p.: 154°–156° C. (methyl cyanide).

Index of rotation ($[c]^{21°}$ C. = 1% in DMSO):

| λnm | α° |
| --- | --- |
| 589 | +29.2 |
| 578 | +31.1 |
| 546 | +38.1; |

19) d-2-{[2-(2-(N-isoquinol-1-ylmethylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate, m.p.: 126°–128° C.

Index of rotation ($[c]^{23°}$ C. = 1% in DMSO):

| λnm | α° |
| --- | --- |
| 589 | +28.3 |
| 578 | +30.2 |
| 546 | +37.6; |

20) d-2-{2-[[2-(2-(N-pyrid-2-yl)ethylamino)ethoxy]ethoxy]methyl}-4-(2,3-dichlorophenyl)-3-ethoxycarbonyl-5-methoxycarbonyl-6-methyl-1,4-dihydropyridine and its dihydrochloride in the form of a lyophilisate.

Index of rotation ($[c]^{21°}$ C. = 1% in DMSO):

| λnm | α° |
| --- | --- |
| 589 | +31.03 |
| 578 | +33.2 |
| 546 | +41.2; |

21) d-2-{[2-(2-[N-(N-methylindol-3-yl)methylamino]ethoxy)ethoxy]methyl}-4-(2,3-dichlorophenyl)-3-ethoxycarbonyl-5-methoxycarbonyl-6-methyl-1,4-dihydropyridine and its monoethyl oxalate, m.p.: 140°–142° C. (CH3CN).

22) d-2-{[2-(2-[N-(indol-3-yl)methylamino]ethoxy)ethoxy]methyl}-4-(2,3-dichlorophenyl)-3-ethoxycarbonyl-5-methoxycarbonyl-6-methyl-1,4-dihydropyridine and its hydrochloride in the form of a lyophilisate.

23) d-2-{[2-(2-[N-(quinol-3-yl)methylamino]ethoxy)ethoxy]methyl}-4-(2,3-dichlorophenyl)-3-ethoxycarbonyl-5-methoxycarbonyl-6-methyl-1,4-dihydropyridine and its monoethyl oxalate, m.p.: 136°–138° C. (CH3CN).

Index of rotation ($[c]^{21°}$ C. = 1% in DMSO):

| λnm | α° |
| --- | --- |
| 589 | +29.2 |
| 578 | +31.2 |
| 546 | +38.6 |
| 436 | +128.9; |

24) d-2-{{2-[2-[N-(benzofurazan-5-ylmethyl)amino]ethoxy]ethoxy}methyl}-4-(2,3-dichlorophenyl)-3-ethoxycarbonyl-5-methoxycarbonyl-6-methyl-1,4-dihydropyridine and its monoethyl oxalate, m.p.: 146°–148° C. (CH3CN).

Index of rotation ($[c]^{22°}$ C. = 1% in DMSO):

| λnm | α° |
| --- | --- |
| 589 | +27.5 |
| 578 | +29.7 |
| 546 | +37.1 |
| 436 | +130.5; |

25) d-2-{{2-[2-[N-(benzofurazan-4-ylmethyl)amino]ethoxy]ethoxy}methyl}-4-(2,3-dichlorophenyl)-3-ethoxycarbonyl-5-methoxycarbonyl-6-methyl-1,4-dihydropyridine.

26) d-2-{{2-[2-[N-(benzo-2,1,3-thiadiazol-5-ylmethyl)amino]ethoxy]ethoxy}methyl}-4-(2,3-dichlorophenyl)-3-ethoxycarbonyl-5-methoxycarbonyl-6-methyl-1,4-dihydropyridine.

27) d-2-{{2-[2-[N-(benzo-2,1,3-thiadiazol-4-ylmethyl)amino]ethoxy]ethoxy}methyl}-4-(2,3-dichlorophenyl)-3-ethoxycarbonyl-5-methoxycarbonyl-6-methyl-1,4-dihydropyridine.

EXAMPLE 28 d-2-{[2-(2-[N-dibenzo[a,d]cyclohept-5-ylamino)ethoxy)ethoxy]methyl}-4-(2,3-dichlorophenyl)-3-ethoxycarbonyl-5-methoxycarbonyl-6-methyl-1,4-dihydropyridine 0.01 mol of d-2-{[2-(2-aminoethoxy)ethoxy]methyl}-4-(2,3-dichlorophenyl)-3-ethoxycarbonyl-5-methoxycarbonyl-6-methyl-1,4-dihydropyridine, 0.01 mol of potassium carbonate, 0.1 g of potassium iodide and 0.01 mol of 5-chlorodibenzo[a,d]cycloheptane in 40 ml of acetonitrile are heated at reflux with stirring for one night. After dilution with water and extraction, the evaporated residue is purified by flash chromatography (eluant: CHCl3 in alcohol/CH3COOC2H5, 75/25). d-2-{[2-(2-[N-dibenzo[a,d]cyclohept-5-ylamino)ethoxy)e- thoxy]methyl}-4-(2,3-dichlorophenyl)-3-ethoxycarbonyl-5-methoxycarbonyl-6-methyl-1,4-dihydropyridine is obtained in that manner in a yield of 31%.

0.0029 mol of the base so obtained is dissolved in 20 ml of acetonitrile. 1 ml of 3N ethereal hydrogen chloride is added thereto and the whole is then evaporated to dryness.

In that manner 1.8 g of the hydrochloride of the [+] isomer of 2-{[2-(2-(N-dibenzo[a,d]cyclohept-5-ylamino)ethoxy)ethoxy]methyl}-4-(2,3-dichlorophenyl)-3-ethoxycarbonyl-5-methoxycarbonyl-6-methyl-1,4-dihydropyridine are obtained, m.p.: 160°–162° C. (ethyl acetate). Yield: 86%.

Index of rotation ($[c]^{21°\ C.} = 1\%$ in DMSO):

| λnm | α° |
| --- | --- |
| 589 | +27.6 |
| 578 | +29.6 |
| 546 | +36.7. |

EXAMPLE 29 d-2-{{2-[2-[N-methyl-N-(pyrid-4-ylmethyl)amino]ethoxy]ethoxy}methyl}-4-(2,3-dichlorophenyl)-3-ethoxycarbonyl-5-methoxycarbonyl-6-methyl-1,4-dihydropyridine

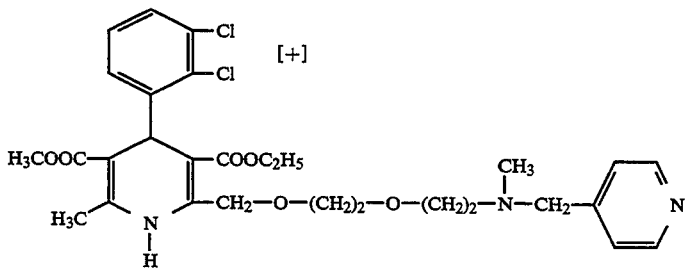

0.14 mol of d-2-{{2-[2-[N-pyrid-4-ylmethylamino]ethoxy]ethoxy}methyl}-4-(2,3-dichlorophenyl)-3-ethoxycarbonyl-5-methoxycarbonyl-6-methyl-1,4-dihydropyridine with 0.035 mol of trimethyl phosphate is maintained at 65° C. for 4 hours with stirring. The whole is taken up in ethyl acetate, washed with sodium hydrogen carbonate and then with water and extracted with normal hydrochloric acid, the acidic phases are rendered basic in the cold and then an extraction with ethyl acetate is carried out.

The evaporated residue is subjected to flash chromatography (CH₂Cl₂—CH₃OH) (97-3). The desired product is obtained in the form of an oil. Yield: 18%.

The base is converted into a salt with 2 equivalents of oxalic acid in ethanol. After filtration of the precipitate and recrystallisation from acetonitrile, the dioxalate of d-2-{{2-[2-[N-methyl-N-(pyrid-4-ylmethyl)amino]ethoxy]ethoxy}methyl}-4-(2,3-dichlorophenyl)-3-ethoxycarbonyl-5-methoxycarbonyl-6-methyl-1,4-dihydropyridine is obtained, m.p.: 110°–112° C. (CH₃CN).

Index of rotation ($[c]^{21.6°\ C.} = 1\%$ in DMSO):

| λnm | α° |
| --- | --- |
| 589 | +24.2 |
| 578 | +25.5 |
| 546 | +32.2. |

EXAMPLE 30

Pharmacological Study

Resistance to anticancer agents is a major obstacle to the effectiveness of antitumour drugs. Of the different types of resistance, "Multidrug Resistance" (MDR) is of particular importance, since it is induced by compounds of natural origin which are active against solid tumours (anthracyclines, vinca alkaloids, epipodophyllotoxins for example), and is very frequent in certain cancers (colon, for example). When tumour cells are exposed in vitro or in vivo to one of those drugs they become resistant, to varying degrees, to all of those compounds. The phenomenon of resistance is as a result of the action of an inducible membrane protein, gP 170, the role of which is to increase the efflux of the cytotoxic agent, thus reducing its intracellular concentration, which results in the loss of sensitivity of those cells to the drug.

Some medicaments used in other pathologies are known to reverse the resistance of tumour cells partially or completely (Tsuruo T., Mechanisms of multidrug resistance and implications for therapy. Int. J. Cancer Res., 79, 285–296, 1988; Rothenberg, M. and Ling V., Multidrug resistance: molecular biology and clinical relevance, J.N.C.I., 81, 907–910, 1989; Gottesman M. M. and Pastan I., Resistance to multiple chemotherapeutic agents in human cancer cells, Trends Pharmacol. Sci., 9, 54–58, 1989; Endicott J. A. and Ling V., The biochemistry of P-glycoprotein-mediated multidrug resistance, Annu. Rev. Biochem., 58, 137–171, 1989).

When the modulating agent is added at the same time as the cytotoxic agent, it reduces or completely suppresses the resistance to antitumour agents. Certain medicaments, such as verapamil, amiodarone or cyclosporin, have been used clinically to overcome that resistance, but their intrinsic pharmacological properties and their toxicity limit their use considerably. This gave rise to the interest in searching for compounds that increase the sensitivity of resistant tumour cells but that do not have other undesirable pharmacological properties and that are non-toxic. In the case of dihydropyridines, it is necessary to increase the reversing activity and to decrease the calcium channel-blocking properties.

Moreover, the mechanism of the resistance to chloroquine developed by Plasmodium falciparum is similar. Verapamil restores the sensitivity of a line resistant to chloroquine (Krogstad D. J., Gluzman I. Y., Kule D. E., Oduola A. M. J., Martin S. K., Milhous W. K., Schlessinger P. H., Efflux of Chloroquine from Plasmodium falciparum: mechanism of chloroquine resistance, Science, 238, 1283–1285, 1987; Martin S. K., Oduola A. M. J., Milhous W. K., Reversal of Chloroquine resistance in Plasmodium falciparum by Verapamil, Science, 235, 899–901, 1987), as well as amlodipine (Deloron P., Basco L. K., Dubois B., Gaudin C., Clavier F., Le Bras J., Verdier F., In vitro and in vivo potentiation of chloroquine against malaria parasites by an enantiomer of amlodipine, Antimicrobial agents and chemotherapy, vol 35, No. 7, 1338–1342, 1991), which demonstrates the potential value for use in parasitology of compounds that reverse the resistance of tumour cells.

The pharmacological study of the compounds of the present invention consisted first of all in an examination in vitro carried out on resistant cells.

The parameter measured is the cytotoxicity of the antitumour drug, quantified in the absence and in the presence of the reversing compound.

Also measured was the effect of the compounds on the intracellular concentration of adriamycin.

In fact, the known compounds used to reverse MDR act by increasing the intracellular concentration of cytotoxic agent. This effect is the consequence of inhibiting the action of gP 170, which is responsible for the efflux of the drug.

This study was completed by an in vivo study, using a murine leukaemia resistant to vincristine (P 388/VCR) and using the compounds of the present invention in association with vincristine.

At the same time the affinity of the products for the calcium channel was examined.

A/ STUDY ON RESISTANT AND NON-RESISTANT TUMOUR CELLS

Material and Methods

1) Activity in vitro
Cytotoxicity
Two resistant cell lines were used:
 1 Human epidermoid carcinoma, KB-A1, the resistance of which was induced by adriamycin (ADR). Its resistance factor is approximately 300 related to the sensitive line (mean resistance).
 1 Chinese hamster lung line, DC-3F/AD, the resistance of which was induced by actinomycin D. Its resistance factor is greater than 10,000, and it is thus an extremely resistant line. These two lines are also resistant to vinca alkaloids (vincristine and vinblastine).

The cells are cultivated in a complete culture medium (RPMI 1640), containing 10% fetal calf serum, 2 mM glutamine; 50 units/ml penicillin, 50 µg/ml streptomycin, 10 mM Hepes.

The cells are distributed on microplates and exposed to the cytotoxic compounds (actinomycin D for line DC-3F/AD and adriamycin for line KB-A1) at 9 concentrations (2 fold serial dilutions). The compounds tested for their capacity to reverse the resistance are added at the same time as the cytotoxic agent.

The cells are then incubated for 4 days. The number of viable cells is then quantified by a colorimetric assay, the Microculture Tetrazolium Assay (Carmichael J., DeGraff W. G., Gazdar A. F., Minna J. D. and Mitchell J. R., Evaluation of a tetrazolium-based semiautomated colorimetric assay: assessment of chemosensitivity testing, Cancer Res., 47, 936–942, 1987). The results are expressed as $IC_{50}$, the concentration of cytotoxic agent that inhibits the proliferation of treated cells by 50% compared with the control cells.

The results are expressed as a reversion factor (RF):

$$RF = \frac{IC_{50} \text{ cytotoxic agent only}}{IC_{50} \text{ cytotoxic agent in the presence of the reversing compound}}$$

Flow Cytometry

Some anticancer compounds, such as adriamycin (ADR), exhibit the property of being fluorescent after excitation by a light source of known wavelength.

By measuring that fluorescence, it is thus possible to obtain a relative measurement of the intracellular concentration of ADR. Flow cytometry (FCM) is a preferred method of carrying out this kind of measurement and thus determining quickly if certain active compounds act by increasing the intracellular concentration of ADR.

The cells ($5 \times 10^5$ per ml) were exposed simultaneously to ADR at a fixed concentration (50 µM) and to the tested compounds at various concentrations. After 5 hours' incubation, the intracellular accumulation of ADR was evaluated by FCM. The analyses were carried out on a flow cytometer ATC3000 (BRUKER-FRANCE) fitted with a 2025 argon laser (SPECTRA-PHISICS-FRANCE) optimised at 488 nm for a power of 600 mW.

The analysis of each of the samples was carried out on a total of 10,000 cells at a rate of 1,000 cells per second.

The results were presented in the form of linear histograms of the intracellular ADR fluorescence.

Expression of the results: for each of the histograms the mean fluorescence per channel (MEAN) was determined by the computer of the apparatus. For all experiments:
  a negative control (cells without ADR) fixed the autofluorescence threshold.
  a positive control (cells with ADR) determined the MEAN value=MN1.
  the "test" tubes (cells with ADR and with compound) were used to determine, for each of the compounds and at each of the concentrations, the MEAN values=MN2.

The results are expressed in the form of variations from the mean fluorescence obtained for each of the "test" tubes (MN2) in relation to the mean fluorescence obtained with the positive control (MN1): VAR—MEAN=MN2−MN1. The measured parameter is thus the increase in ADR fluorescence in the presence of the tested compounds.

2) Activity in vivo
Antitumour Activity

The sensitive parent line P 388 (murine leukaemia) and the sub-line resistant to vincristine, P 388/VCR, were supplied by NCI (Frederick, USA). The tumour cells ($10^6$ cells) were inoculated on day 0 into the indraperitoneal cavity of female B6D2F1 mice (Iffa Credo, France) weighing from 18 to 20 g (groups of 8 to 10 animals).

Every day for 4 days, starting from day 1, the animals received:
  an administration of 25 to 150 mg/kg by i.p., p.o. or i.v. route of the compound of the present invention to be tested, as mentioned in the table 4a; then
  30 to 60 minutes later, an administration by the i.p. route of 0.25 mg/kg of vincristine (used as a reference antitumour agent).

The antitumour activity is expressed as follows:

$$\frac{T}{C}\% = \frac{\text{Median survival time of the treated animals}}{\text{Median survival time of the control animals}} \times 100$$

The values are mean values obtained in independent experiments (# sem when n is greater than or equal to 3).

RESULTS

1) Activity in vitro

Cytotoxicity

Table 1 gives the reversion factor values obtained with the various compounds using the line DC-3F/AD and Table 2 using the line KB-A1.

All of the tested compounds of the Examples of the present invention are much more active than the reference compounds, and some of them completely reverse the resistance of KB-A1 cells.

Flow Cytometry

Table 3 gives the increase in the ADR fluorescence (VAR-MEAN) obtained with the various compounds using the line KB-A1.

All of the tested compounds of the Examples of the invention are more active than the reference compounds.

2) Activity in vivo

Tables 4a and 4b show the increase in antitumour activity of vincristine in vivo obtained with various representative compounds of the present invention All of the tested compounds of the Examples of the invention substantially increase the antitumour activity of vincristine in resistant cells, restoring a sensitivity approaching that of sensitive cells.

Using the sensitive line (P388) the tested compounds of the invention increase considerably the sensitivity of the cells to vincristine.

TABLE 1

REVERSION FACTORS USING THE LINE DC-3F/AD

| COMPOUNDS | 1 μM | 2.5 μM | 5 μM |
|---|---|---|---|
| Reference compounds | | | |
| VERAPAMIL | 1.0 | 1.5 | 3.1 |
| NIFEDIPINE | 1.2 | 2.3 | 5.8 |
| AMLODIPINE | 1.0 | 1.4 | 2.6 |
| NK 250 | 1.1 | 1.3 | 2.0 |
| Compounds of the Examples | | | |
| 1 | 21.0 | 1,042.7 | 2,613.2 |
| 2 | 1.5 | 141.3 | 1,478.2 |
| 4 | 23.0 | 294.4 | 3,962.3 |
| 5 | 7.6 | 267.2 | 3,567.0 |
| 6 | 9.6 | 599.8 | 4,340.9 |
| 8 | 11.4 | 195.6 | 1,319.9 |
| 9 | 1.2 | 53.9 | 560.3 |
| 11 | 1.0 | 394.8 | 2,442.4 |
| 12 | 1.1 | 86.1 | 1,320.1 |
| 13 | 19.4 | 622.7 | 4,141.7 |
| 14 | 8.2 | 482.7 | 4,463.2 |
| 15 | 301.4 | 4,375.5 | 6,510.3 |
| 16 | 3.4 | 445.1 | 8,248.4 |
| 17 | 3.7 | 706.1 | 8,600.0 |
| 18 | 3.3 | 1,082.1 | 5,018.4 |
| 19 | 1.5 | 305.7 | 1,701.7 |
| 23 | 10.2 | 310.0 | 2,304.0 |
| 28 | 1.4 | 21.5 | 447.3 |

TABLE 2

REVERSION FACTORS USING THE LINE KB-A1

| COMPOUNDS | 1 μM | 2.5 μM | 5 μM |
|---|---|---|---|
| Reference compounds | | | |
| VERAPAMIL | 4.6 | 16.7 | 26.0 |
| NIFEDIPINE | 1.0 | 1.0 | 1.0 |
| AMLODIPINE | 1.5 | 2.4 | 5.9 |
| NK 250 | 0.8 | 2.3 | 3.1 |
| Compounds of the Examples | | | |
| 1 | 32.1 | 210.6 | 640.5 |
| 2 | 2.2 | 90.6 | 389.5 |
| 4 | 26.0 | 106.4 | 473.7 |
| 5 | 13.2 | 96.5 | 225.8 |
| 6 | 15.2 | 54.7 | 159.1 |
| 8 | 6.9 | 28.2 | 136.0 |
| 9 | 2.4 | 41.8 | 99.0 |
| 11 | 1.7 | 126.3 | 336.0 |
| 12 | 1.2 | 47.0 | 125.4 |
| 13 | 12.3 | 66.8 | 165.1 |
| 14 | 22.7 | 88.0 | 169.4 |
| 15 | 12.1 | 65.3 | 281.9 |
| 16 | 13.9 | 49.2 | 122.4 |
| 17 | 10.5 | 45.7 | 120.7 |
| 18 | 4.3 | 193.3 | 348.2 |
| 19 | 3.6 | 40.3 | 140.5 |
| 23 | 19.6 | 101.2 | 1,035.8 |

TABLE 3

MEASUREMENT OF THE INTRACELLULAR ACCUMULATION OF ADR LINE KB-A1

| COMPOUNDS | CONCENTRATION (μM) | | |
|---|---|---|---|
| | 1 | 2.5 | 5 |
| Reference compounds | | | |
| VERAPAMIL | 3.7 | 8.6 | 12.2 |
| NIFEDIPINE | 0.0 | 0.0 | 0.0 |
| AMLODIPINE | 0.0 | 2.1 | 4.7 |
| Compounds of Examples | | | |
| 1 | 5.5 | 26.1 | 45.7 |
| 4 | 2.0 | 7.0 | 18.6 |
| 8 | 2.0 | 9.4 | 24.2 |
| 11 | 0.2 | 18.2 | 31.0 |
| 14 | 2.4 | 8.2 | 20.5 |
| 15 | 7.0 | 16.1 | 38.6 |
| 19 | 9.4 | 15.7 | 34.7 |

TABLE 4a

INCREASE IN THE ANTITUMOUR ACTIVITY OF VINCRISTINE CAUSED BY PRODUCTS OF THE PRESENT INVENTION USING THE RESISTANT LINE P 388/VCR

| VCR i.p. | COMPOUNDS OF THE EXAMPLES | | | T/C % |
|---|---|---|---|---|
| | Examples | Dose | Route | |
| 0.25 mg/kg | — | — | — | 150 |
| 0 | 1 | 50 mg/kg | i.p | 107 |
| 0 | 1 | 150 mg/kg | p.o | 99 |
| 0.25 mg/kg | 1 | 50 mg/kg | i.p | 171 |
| 0.25 mg/kg | 1 | 150 mg/kg | p.o | 185 |
| 0 | 4 | 50 mg/kg | i.p | 100 |
| 0 | 4 | 150 mg/kg | p.o | 110 |
| 0.25 mg/kg | 4 | 50 mg/kg | i.p | 176 |
| 0.25 mg/kg | 4 | 150 mg/kg | p.o | 181 |
| 0 | 11 | 50 mg/kg | i.p | 100 |
| 0 | 11 | 150 mg/kg | p.o | 99 |
| 0.25 mg/kg | 11 | 50 mg/kg | i.p | 146 |
| 0.25 mg/kg | 11 | 150 mg/kg | p.o | 177 |
| 0 | 14 | 50 mg/kg | i.p | 99 |
| 0 | 14 | 150 mg/kg | p.o | 103 |
| 0.25 mg/kg | 14 | 50 mg/kg | i.p | 164 |
| 0.25 mg/kg | 14 | 150 mg/kg | p.o | 200 |
| 0 | 15 | 25 mg/kg | i.p | 109 |

TABLE 4a-continued

INCREASE IN THE ANTITUMOUR ACTIVITY OF VINCRISTINE CAUSED BY PRODUCTS OF THE PRESENT INVENTION USING THE RESISTANT LINE P 388/VCR

| VCR i.p. | COMPOUNDS OF THE EXAMPLES | | | T/C % |
|---|---|---|---|---|
| | Examples | Dose | Route | |
| 0 | 15 | 25 mg/kg | p.o | 112 |
| 0 | 15 | 25 mg/kg | i.v | 94 |
| 0.25 mg/kg | 15 | 25 mg/kg | i.p | 262 |
| 0.25 mg/kg | 15 | 25 mg/kg | p.o | 180 |
| 0.25 mg/kg | 15 | 25 mg/kg | i.v | 186 |
| 0 | 28 | 50 mg/kg | i.p | 107 |
| 0 | 28 | 150 mg/kg | p.o | 99 |
| 0.25 mg/kg | 28 | 50 mg/kg | i.p | 180 |
| 0.25 mg/kg | 28 | 150 mg/kg | p.o | 207 |

TABLE 4b

| VCR i.p. | COMPOUND OF THE EXAMPLES | | | T/C % | Survivors on day 60 |
|---|---|---|---|---|---|
| | Examples | Dose | Route | | |
| 0.25 mg/kg | — | — | — | 239 | 0/8 |
| 0 | 1 | 150 mg/kg | p.o. | 99 | 0/8 |
| 0.25 mg/kg | 1 | 150 mg/kg | p.o. | >532 | 4/8 |
| 0 | 8 | 150 mg/kg | p.o. | 106 | 0/8 |
| 0.25 mg/kg | 8 | 150 mg/kg | p.o. | 294 | 2/8 |
| 0 | 14 | 150 mg/kg | p.o. | 95 | 0.8 |
| 0.25 mg/kg | 14 | 150 mg/kg | p.o. | >587 | 4/8 |
| 0 | 15 | 12.5 mg/kg | p.o. | 101 | 0/8 |
| 0.25 mg/kg | 15 | 12.5 mg/kg | p.o. | 540 | 3/8 |

B/ AFFINITY OF THE COMPOUNDS OF THE INVENTION FOR THE CALCIUM CHANNEL LABELLED WITH [³] PN 200110

The tests were carried out with pig aorta smooth muscle microsome preparations in accordance with the experimental conditions described by A. GOLL (FEBS Lett. 1983, 157, 63–9).

The results are expressed as IC$_{50}$ (M) and represent means of three independent experiments. They are listed in Table 5.

TABLE 5

| COMPOUNDS | IC$_{50}$ (M) |
|---|---|
| Example | |
| 1 | $1.6 \times 10^{-6}$ |
| 12 | $1.3 \times 10^{-6}$ |
| 14 | $1.0 \times 10^{-6}$ |
| 16 | $1.6 \times 10^{-6}$ |
| 17 | $1.4 \times 10^{-6}$ |
| 18 | $1.1 \times 10^{-6}$ |
| 19 | $3.2 \times 10^{-6}$ |
| 20 | $2.1 \times 10^{-6}$ |
| 22 | $3.3 \times 10^{-6}$ |
| 23 | $2.0 \times 10^{-6}$ |
| NIFEDIPINE | $2.5 \times 10^{-8}$ |

These results show that, in contrast to nifedipine, the compounds of the invention have only a low affinity for the calcium channel and are therefore very weak calcium channel-blocking agents.

SUMMARY

The results listed in Tables 1 to 5 together show that the compounds of the present invention:
have a weak calcium channel-blocking activity, 100 times weaker than that of the reference compound,
are of low toxicity, even when administered to mice at strong doses for 4 days,
substantially increase, in vitro, the sensitivity of cells that are resistant to antitumour agents, including cells exhibiting the MDR phenotype, and do so at micromolar concentrations,
substantially increase the accumulation of adriamycin in resistant cells,
substantially increase the survival of animals bearing resistant leukaemia (P388/VCR) (when administered at the same time as vincristine),
increase the effectiveness, in vivo, of antitumour agents on sensitive cells, thereby increasing the number of survivors in the treated groups. This results in the possibility of reducing the doses of cytotoxic medicaments used in association.

CONCLUSION

According to the pharmacological study carried out, the compounds of the present invention increase substantially the sensitivity of tumour cells to antitumour agents, whether those cells have or have not acquired a resistance to various antitumour agents, and at the same time exhibit only very weak calcium channel-blocking properties as a result of which they do not have a hypotensive effect. The said compounds may consequently be used therapeutically, and in particular in anticancer therapy, without causing undesirable side effects.

We claim:

1. A 1,4-dihydropyridine compound selected from those of formula I:

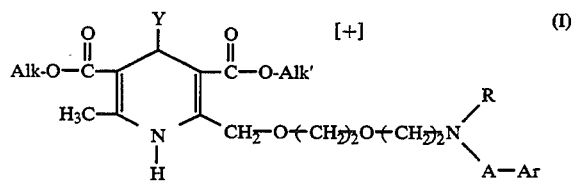

wherein:
Y represents phenyl which is optionally substituted by 1 to 5 identical or different substituents, each being halogen, alkoxy, or alkylthio, each having 1 to 4 carbon atoms inclusive, trihalomethyl, or methylenedioxy;

Alk and Alk', which are the same or different, each represents straight-chain or branched alkyl having 1 to 5 carbon atoms inclusive;

R represents hydrogen, straight-chain or branched alkyl having 1 to 5 carbon atoms inclusive, or straight-chain or branched alkenyl or alkynyl, each having 3 to 5 carbon atoms inclusive;

A represents:
—(CH$_2$)$_m$— in which m is an integer of 1 to 5 inclusive, optionally substituted by a substituent selected from: straight-chain and branched alkyl having 1 to 5 carbon atoms inclusive, and straight-chain and branched alkenyl and alkynyl each having 2 to 5 carbon atoms inclusive, and simultaneously Ar represents:
a) phenyl which is substituted by one or more halogen, trifluoromethyl, nitro, cyano, or alkoxycarbonyl having 2 to 6 carbon atoms inclusive or alkylthio having 1 to 5 carbon atoms, inclusive b) thienyl, pyridyl, naphthyl, quinolyl, isoquinolyl, indolyl, N-methylindolyl, benzofurazanyl, or benzo-2,1,3-thiadiazolyl, or the whole of —A—Ar represents dibenzo[a,d]cyclohept-5-yl; in the form of the dextrorotatory isomer, and its physiologically tolerable addition salts with a pharmaceutically-acceptable acid.

2. A compound of claim 1 which is: selected from d-2-{[2-(2-(N-p-nitrobenzylamino)ethoxy)ethoxy]methyl}-4-(2,3-dichlorophenyl)-3-ethoxycarbonyl-5-methoxycarbonyl-6-methyl-1,4-dihydropyridine, its monoethyl oxalate, and its hydrochloride.

3. A compound of claim 1 which is: selected from d-2-{[2-(2-(N-p-cyanobenzylamino)ethoxy)ethoxy]methyl}-4-(2,3-dichlorophenyl)-3-ethoxycarbonyl-5-methoxycarbonyl-6-methyl-1,4-dihydropyridine, and its monoethyl oxalate.

4. A compound of claim 1 which is: selected from d-2-{[2-(2-(N-thien-3-ylmethylamino)ethoxy)ethoxy]methyl}-4-(2,3-dichlorophenyl)-3-ethoxycarbonyl-5-methoxycarbonyl-6-methyl-1,4-dihydropyridine, its monoethyl oxalate, and its fumarate.

5. A compound of claim 1 which is: selected from d-2-{[2-(2-(N-pyrid-4-ylmethylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate.

6. A compound of claim 1 which is: selected from d-2-{[2-(2-(N-quinol-4-ylmethylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate.

7. A compound of claim 1 which is: selected from d-2-{[2-(2-(N-p-fluorobenzylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate.

8. A compound of claim 1 which is: selected from d-2-{[2-(2-(N-naphth-1-ylmethylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate.

9. A compound of claim 1 which is: selected from d-2-{[2-(2-(N-o-nitrobenzylamino)ethoxy)ethoxy]methyl}-4-(2,3-dichlorophenyl)-3-ethoxycarbonyl-5-methoxycarbonyl-6-methyl-1,4-dihydropyridine and its monoethyl oxalate.

10. A compound of claim 1 which is: selected from d-2-{{2-[2-[N-(benzofurazan-5-ylmethyl)amino]ethoxy]ethoxy}methyl}-4-(2,3-dichlorophenyl)-3-ethoxycarbonyl-5-methoxycarbonyl-6-methyl-1,4-dihydropyridine and its monoethyl oxalate.

11. A compound of claim 1 which is: selected from d-2-{{2-[2-[N-methyl-N-(pyrid-4-ylmethyl)amino]ethoxy]ethoxy}methyl}-4-(2,3-dichlorophenyl)-3-ethoxycarbonyl-5-methoxycarbonyl-6-methyl-1,4-dihydropyridine and its dioxalate.

12. A Pharmaceutical composition useful for potentiating the activity of cytotoxic agents and increasing the sensitivity of tumour cells to antitumour agents, comprising as active ingredient an effective amount of at least one compound as claimed in claim 1 together with one or more pharmaceutically-acceptable excipients.

13. A method for treating a living animal body afflicted with a pathology, for the treatment of which it is desirable to potentiate the activity of cytotoxic agents or to increase the sensitivity of tumor cells to antitumor agents, comprising the step of administering to the said body an amount of a 1,4-dihydropyridine compound selected from those of formula I:

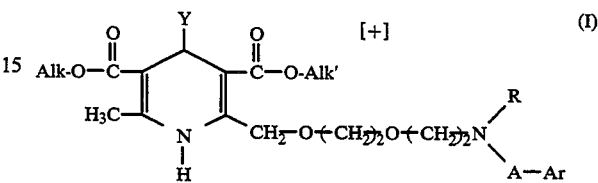

wherein:
Y represents phenyl which is optionally substituted by 1 to 5 identical or different substituents, each being halogen, alkoxy, or alkylthio, each having 1 to 4 carbon atoms inclusive, trihalomethyl, or methylenedioxy;

Alk and Alk', which are the same or different, each represents straight-chain or branched alkyl having 1 to 5 carbon atoms inclusive;

R represents hydrogen, straight-chain or branched alkyl having 1 to 5 carbon atoms inclusive, or straight-chain or branched alkenyl or alkynyl, each having 3 to 5 carbon atoms inclusive;

A represents:
(CH$_2$)$_m$— in which m is an integer of 1 to 5 inclusive, optionally substituted by a substituent selected from:
straight-chain and branched alkyl having 1 to 5 carbon atoms inclusive, and straight-chain and branched alkenyl and alkynyl each having 2 to 5 carbon atoms inclusive, and simultaneously Ar represents:
a) phenyl which is optionally substituted by one or more halogen, trifluoromethyl, nitro, cyano or alkoxycarbonyl having 2 to 6 carbon atoms inclusive or alkylthio having 1 to 5 carbon atoms, inclusive, b) thienyl, pyridyl, naphthyl, quinolyl, isoquinolyl, indolyl, N-methylindolyl, benzofurazanyl, or benzo-2,1,3-thiadiazolyl, or the whole of —A—Ar represents dibenzo[a,d]cyclohept-5-yl; in the form of the dextrorotatory isomer, which is effective for the said purpose.

* * * * *

UNITED STATES PATENT AND TRADEMARK OFFICE
CERTIFICATE OF CORRECTION

PATENT NO. : 5,389,644

DATED : February 14, 1995

INVENTOR(S) : Jean-Louis Peglion, Ghanem Atassi, Alain Pierre, Laurence Kraus-Berthier, Nicolas Guilbaud, Jean-Paul Vilaine It is certified that error appears in the above-indentified patent and that said Letters Patent is hereby corrected as shown below:

```
TITLE PAGE, ITEM [75] Inventors; "Ghanem Aasssi" should read
     -- Ghanem Atassi --
Column 10, line 20; "methyl)-4-" should read -- methyl}-4- --
Column 12, line 68; delete the "e" at the end of the line,
     leaving the hyphen.
Column 13, line  1; "thoxy]" should read -- ethoxy] --
Column 16, line 57; "draperitoneal" should read
     -- traperitoneal --

Column 19, line 35; "[³]" should read -- [³H] --
Column 21, line  6; delete the ":" after the word "is" and
     insert ":" after the word "from" (Prel.Amdt.2-4-93)
Column 21, line 11; delete the ":" after the word "is" and
     insert ":" after the word "from" (Prel.Amdt.2-4-93)
Column 21, line 16; delete the ":" after the word "is" and
     insert ":" after the word "from" (Prel.Amdt.2-4-93)
Column 21, line 21; delete the ":" after the word "is" and
     insert ":" after the word "from" (Prel.Amdt.2-4-93)
Column 21, line 26; delete the ":" after the word "is" and
     insert ":" after the word "from" (Prel.Amdt.2-4-93)
Column 21, line 31; delete the ":" after the word "is" and
     insert ":" after the word "from" (Prel.Amdt.2-4-93)
Column 21, line 36; delete the ":" after the word "is" and
     insert ":" after the word "from" (Prel.Amdt.2-4-93)
Column 21, line 41; delete the ":" after the word "is" and
     insert ":" after the word "from" (Prel.Amdt.2-4-93)
Column 21, line 46; delete the ":" after the word "is" and
     insert ":" after the word "from" (Prel.Amdt.2-4-93)
```

UNITED STATES PATENT AND TRADEMARK OFFICE
CERTIFICATE OF CORRECTION

PATENT NO. : 5,389,644
DATED : February 14, 1995
INVENTOR(S) : Jean-Louis Peglion, Ghanem Atassi, Alain Pierre, Laurence Kraus-Berthier, Nicolas Guilbaud, Jean-Paul Vilaine It is certified that error appears in the above-indentified patent and that said Letters Patent is hereby corrected as shown below:

```
Column 21, line 51; delete the ":" after the word "is" and
     insert the ":" after the word "from"(Prel. Amdt.2-4-93)
Column 22, line  3; delete the words "as claimed in" and insert
     the word "of" (Prel. Amdt. 2-4-93)
```

Signed and Sealed this

Fourth Day of July, 1995

Attest:

BRUCE LEHMAN

Attesting Officer     Commissioner of Patents and Trademarks